United States Patent [19]

Patel et al.

[11] 4,284,459
[45] Aug. 18, 1981

[54] METHOD FOR MAKING A MOLDED CATHETER

[75] Inventors: Bhupendra C. Patel, Elgin; Russell J. Schweizer, Crystal Lake, both of Ill.; Jesse C. Smith, St. Petersburg Beach, Fla.

[73] Assignee: The Kendall Company, Boston, Mass.

[21] Appl. No.: 115,842

[22] Filed: Jan. 28, 1980

Related U.S. Application Data

[62] Division of Ser. No. 921,696, Jul. 3, 1978, Pat. No. 4,207,900.

[51] Int. Cl.³ .............. B29C 27/00; B29D 23/02; B29G 3/08
[52] U.S. Cl. .............. 156/245; 156/256; 156/294; 264/138; 264/259; 264/275; 264/279; 264/328.1; 264/334
[58] Field of Search .............. 264/138, 248, 259, 250, 264/254, 275, 279, 294, 328.1, 157, 334; 128/349 R, 349 B, 349 BV, 350 R; 156/245, 250, 258, 294, 303.1, 256

[56] References Cited

U.S. PATENT DOCUMENTS

| 2,330,399 | 9/1943 | Winder | 264/250 |
| 2,481,488 | 9/1949 | Auzin | 264/250 |
| 3,291,870 | 12/1966 | Allison | 264/317 |
| 3,304,353 | 2/1967 | Harautuneian | 264/317 |
| 3,460,540 | 8/1969 | Gagne | 128/349 R |
| 3,528,869 | 9/1970 | Dereniuk | 264/248 |
| 3,832,253 | 8/1974 | Di Palma et al. | 156/303.1 |
| 3,850,720 | 11/1974 | Collins | 128/349 R |
| 3,865,666 | 2/1975 | Shoney | 264/250 |
| 3,901,965 | 8/1975 | Honeyman | 264/275 |
| 3,959,429 | 5/1976 | Benning | 264/250 |
| 3,993,080 | 11/1976 | Loseff | 128/350 R |
| 4,154,244 | 5/1979 | Becker et al. | 128/349 B |
| 4,157,094 | 6/1979 | Patel | 128/349 B |
| 4,207,899 | 6/1980 | Patel | 128/349 B |

FOREIGN PATENT DOCUMENTS 2301350  2/1975  France ..................... 264/317
1380991  1/1975  United Kingdom ......... 128/349 B

OTHER PUBLICATIONS

Randolph et al., Plastics Engineering Handbook, Reinhold, N.Y., (1960), pp. 399 & 400.

Primary Examiner—Willard E. Hoag
Attorney, Agent, or Firm—Powell L. Sprunger

[57] ABSTRACT

Method for making a catheter comprising, an elongated shaft having a main lumen extending through the shaft, and an inflation lumen extending through a wall of the shaft. The catheter has a tip molded directly onto a distal end of the shaft, and a connecter molded directly onto a proximal end of the shaft.

17 Claims, 5 Drawing Figures

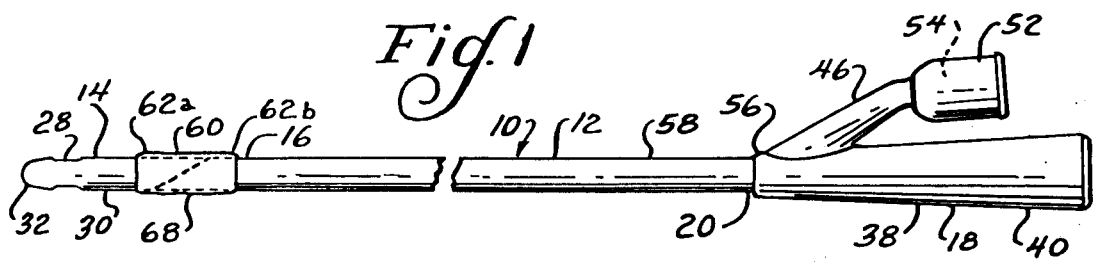
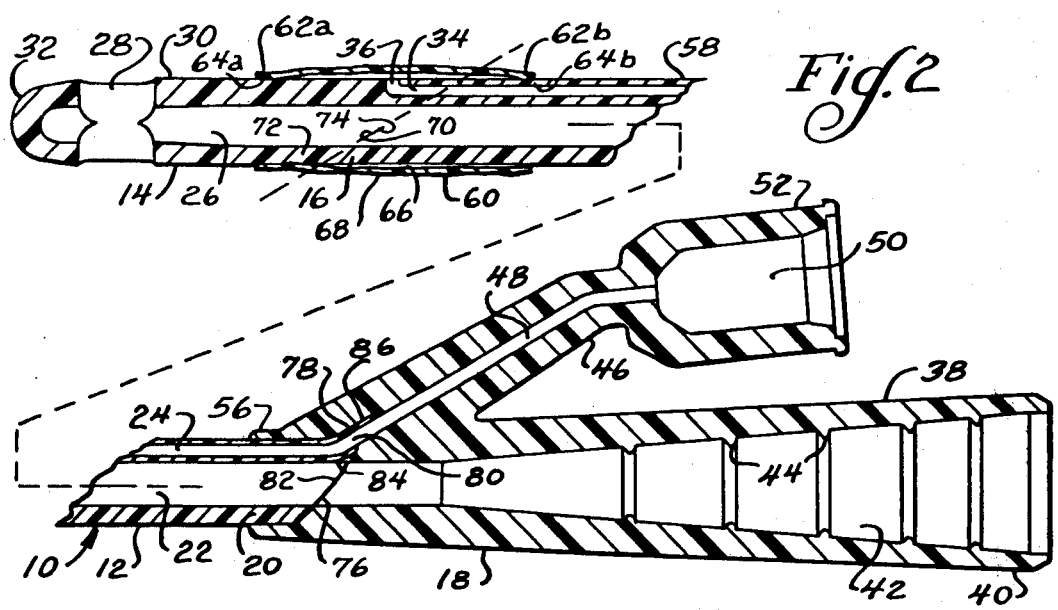
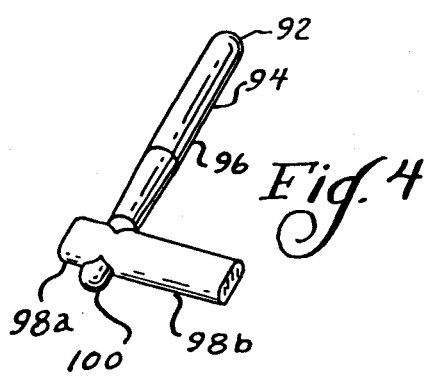
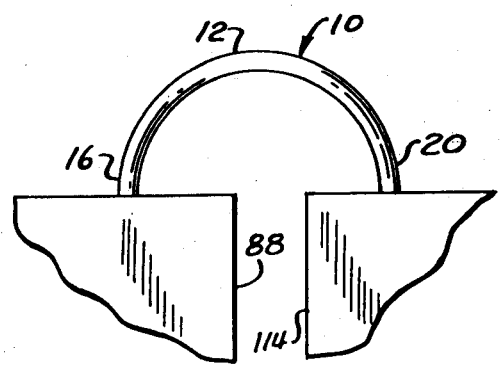

METHOD FOR MAKING A MOLDED CATHETER

This is a division of application Ser. No. 921,696 filed July 3, 1978, and now U.S. Pat. No. 4,207,900.

BACKGROUND OF THE INVENTION

The present invention relates to catheters.

A various assortment of catheters, such as urinary catheters and endotracheal tubes, have been proposed for use in patients. In the case of urinary catheters, Foley catheters are commonly constructed with a shaft having a drainage lumen and an inflatable balloon adjacent a distal end of the shaft. During placement, a distal end of the cathether is passed through the patient's urethra until the balloon and drainage eyes, which communicate with the drainage lumen, are located in the patient's bladder, and the balloon is inflated through an inflation lumen to retain the catheter in place. During catheterization, urine drains through the drainage eyes and lumen and through a drainage tube connected to a proximal end of the catheter to a drainage bag for collection therein.

Conventional catheters of this sort were made from latex rubber through dipping techniques known to the art. In time, it was discovered that the latex catheters were not completely satisfactory since layers of the dipped material occasionally became delaminated during use, thus causing blockage in the inflation lumen and obstructing deflation of the balloon when it was necessary to remove the catheter from the patient. As a result, it became desirable to construct the catheter shaft from a material which may be extruded in order to prevent possible blockage of the inflation lumen, and reduce the cost of the catheter to the patient due to simplified manufacturing techniques.

In turn, the materials which appeared satisfactory for use as a shaft posed new problems in construction of the catheter. For example, it became necessary to find suitable materials for the balloon which are sufficiently elastic to permit inflation during use, and which are compatible with the selected shaft for bonding purposes. Frequently, materials which appeared otherwise satisfactory for the catheter shaft and balloon proved to be incompatible when attempts were made to bond the balloon to the shaft through use of adhesive or sealing. In addition, it became necessary to secure a tip to the distal end of the extruded shaft, and a connecter to the proximal end of the shaft. Such tips and connectors have been formed separately, and have been adhered to the shaft. However, in the case of the connecters, it is necessary to establish communication between lumens in the connecter and the associated inflation and drainage lumens in the shaft. In the case of the tips, it is necessary to obtain a sufficient bond of the tip to the distal end of the shaft while closing the distal end of the inflation lumen. In both cases, difficulties have been encountered in obtaining the proper alignment of lumens and achieving the desired bond. In addition, it has been necessary in the past to separately form an opening in the outer surface of the shaft to obtain communication between the inflation lumen and a cavity beneath the balloon. All of the excessive operations and difficulties associated with construction of the catheter deleteriously affect the capability of providing the catheter, which is considered a disposable item, at a significantly reduced cost.

SUMMARY OF THE INVENTION

A principal feature of the present invention is the provision of a catheter of simplified construction and reduced cost.

The catheter of the present invention comprises, an elongated shaft having a main lumen extending through the shaft, and an inflation lumen extending through a wall of the shaft. The catheter has a tip molded directly onto a distal end of the shaft, with the tip having a lumen communicating with the main lumen of the shaft, and at least one opening adjacent a distal end of the tip communicating with the tip lumen. The molded tip defines a distal end portion of the inflation lumen and an aperture at an outer surface of the tip. The distal end of the shaft and the proximal end of the tip have complementary beveled portions defining juncture surfaces which are bonded together. The catheter has a connecter directly bonded onto a proximal end of the shaft, with the connecter having a lumen communicating with the shaft drainage lumen, and an inflation lumen in a side arm communicating with the inflation lumen of the shaft. The connecter and proximal end of the shaft have complementary beveled portions defining juncture surfaces, and the shaft has a proximal end portion defined by the bevel which is outwardly flared in the molded connecter. The catheter also has a sleeve of elastic material secured to the catheter in spaced circumferential zones and defining a cavity communicating with the inflation lumen.

A feature of the present invention is that the beveled portions at the proximal and distal ends of the catheter shaft define an enlarged surface area to achieve an enhanced bond between the shaft and the catheter tip and connecter.

Another feature of the invention is that the distal end portion of the inflation lumen is automatically formed in the tip during molding of the tip.

A further feature of the invention is that an aperture is defined at the distal end of the inflation lumen in the tip during molding of the tip.

Yet another feature of the invention is that the outwardly flared proximal end portion of the catheter shaft ensures structural continuity and integrity between the inflation lumens of the shaft and connecter.

A feature of the present invention is that the catheter shaft is insert molded onto the tip and connecter in a simplified manner without the use of adhesive.

A further feature of the invention is that the catheter may be made at a reduced cost.

Another feature of the invention is the provision of methods for constructing the catheter of the present invention.

Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary sectional view of the catheter of FIG. 1;

FIG. 4 is a perspective view of a main pin for use in the mold of FIG. 3;

FIG. 6 is a fragmentary schematic view of separate molds being used to simultaneously form a tip and connecter onto a catheter shaft.

DESCRIPTION OF THE PREFERRED EMBODIMENTS

Figure 3:
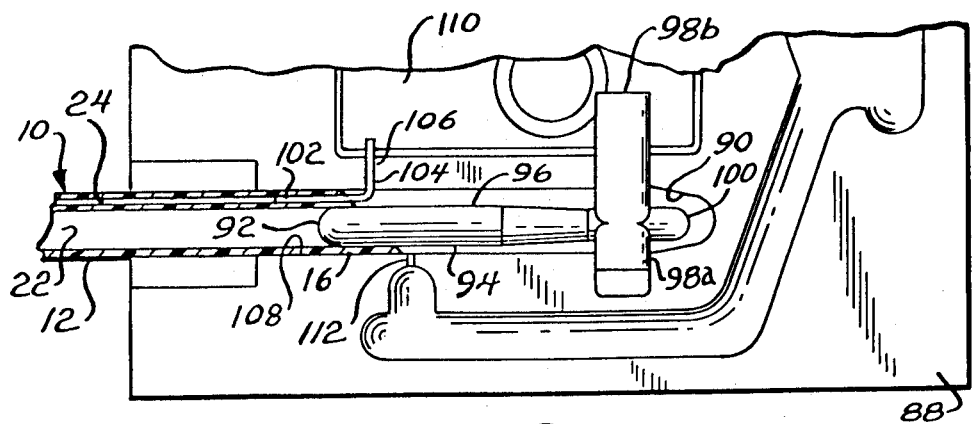
FIG. 3 is a fragmentary plan view of a mold for forming a tip on a distal end of a catheter shaft.

Referring now to FIGS. 1 and 2, there is shown a catheter generally designated 10 having an elongated extruded shaft 12, a tip 14 secured to a distal end 16 of the shaft 12, and a connecter 18 secured to a proximal end 20 of the shaft 12. The shaft 12 has a main or drainage lumen 22 extending through the shaft, and an inflation lumen 24 extending through a wall of the shaft.

The tip 14 has a main lumen 26 communicating with the main lumen 22 of the shaft 12, and a pair of drainage eyes or openings 28 extending to an outer surface 30 of the tip 14, and communicating with the main lumen 26 of the tip. The tip has a closed distal end 32, and the tip defines a distal end portion 34 of the inflation lumen 24 and an aperture 36 at the outer surface 30 of the tip communicating with the lumen portion 34.

The connecter 18 has a connecting portion 38 defining a proximal end 40 of the catheter 10 and defining a main lumen 42 of the connecter 18 communicating with the drainage lumen 22 of the shaft 12. As shown, the proximal end of the connecter lumen 42 is enlarged to receive an adapter of a drainage tube (not shown), and the connecter 18 has a plurality of annular sealing rings 44 in the lumen 42 to snugly engage against the drainage tube adapter. The connecter 18 has a side arm 46 defining an inflation lumen 48 which communicates with the inflation lumen 24 of the shaft 12, and a recess 50 at a proximal end 52 of the side arm 46 to receive suitable valve means 54 for controlling passage of fluid through the inflation lumen of the shaft and connecter. As shown, the connecter 18 has a distal annular flange 56 engaging against an outer surface 58 of the shaft 12 and enclosing the proximal end 20 of the shaft.

The catheter also has an annular sleeve 60 of elastic material forming a balloon adjacent a distal end of the catheter. The sleeve 60 has a pair of opposed ends 62a and 62b which are respectively secured in circumferential zones 64a and 64b to the outer surface 30 of the tip 14 and the outer surface 58 of the shaft 12. In this configuration, the sleeve 60 defines a cavity 66 underlying a central portion 68 of the sleeve 60 which communicates with the inflation lumen through the tip aperture 36.

As shown in FIG. 2, the shaft 12 has a beveled distal end which defines a tapered juncture surface 70 disposed at an acute angle relative to the lower surface of the shaft as shown in the drawing. In turn, the tip 14 has a beveled proximal end 72 which defines a complementary juncture surface 74 disposed at an obtuse angle relative to the lower surface of the shaft as presented in the drawing, with the surfaces 70 and 74 facing each other and being secured together to bond the tip 14 to the shaft 12. As shown, the tip aperture 36 is located intermediate ends of the beveled portions of the tip and shaft.

The shaft 12 also has a beveled proximal end defining a juncture surface 76 disposed at an acute angle relative to an upper surface of the shaft as presented in the drawings, such that the proximal beveled shaft portion defines a tapered end portion 78 containing the proximal end 80 of the shaft inflation lumen 24, with the inflation lumen end 80 being disposed at the apex of the acute angle. The connecter has a complementary beveled juncture surface 82 which is disposed at an obtuse angle relative to the upper surface of the shaft as presented in the drawing. In a preferred form, the acute angles at both the proximal and distal ends of the shaft may range from 30 to 45 degrees. The juncture surfaces 76 and 82 of the shaft 12 and connecter 18 face each other and are secured together inside the connecter 18. As shown, the shaft 12 may be longitudinally severed along a line 84 at the proximal end 20 of the shaft 12, with the line 84 being located intermediate the inflation lumen 24 and the opposed surface of the catheter shaft, such that the severance line 84 defines a flap 86 at the tapered end portion 78 containing the proximal end 80 of the shaft inflation lumen 24. As shown, the flap 86 is outwardly flared in the connecter 18, such that the flap 86 defines a curve in the proximal end 80 of the shaft drainage lumen 24, and spaces the proximal end 80 of the inflation lumen 24 from the main lumens 22 and 42 of the shaft 12 and connecter 18, respectively. In this manner, the outwardly flared flap 86 assures continuity and integrity between the inflation lumen 24 of the shaft 12 and the inflation lumen 48 of the connecter 18 without leakage into the main lumens of the catheter shaft or connecter. However, it is noted that the tapered end portion 78 of the shaft 12 may be placed in the outwardly flared configuration without the severance line 84 due to the tapered configuration of the shaft proximal end 20.

As will be seen below, the tip 14 and connecter 18 are molded directly onto the distal and proximal ends of the shaft, such that the tip and connecter are bonded to the shaft without the use of adhesive. In a preferred form, the shaft 12 and sleeve 60 may be extruded from a suitable elastic material. The tip 14 and connecter 18 may then be molded onto the catheter shaft 12, and the sleeve 60 may be bonded onto the tip and shaft after removal of the catheter from the molds. In a preferred form, the shaft 12 and sleeve 60 may be extruded from the same material of which the tip 12 and connecter 18 are molded, and, in a suitable form, the shaft 12, tip 14, connecter 18, and sleeve 60 may be constructed from a thermoplastic elastomer such as Kraton, a trademark of Shell Oil Company.

Referring now to FIG. 3, there is shown a mold 88 having a cavity 90 for insert molding the distal end 16 of the catheter shaft 12 onto a tip as will be described below. First, the distal end 16 of the catheter shaft 12 is severed at an angle to define the tapered end portion of the cathether shaft. Next, a proximal end 92 of a main pin 94 is inserted into the distal end of the shaft main lumen 22 in order to close the distal end of the main lumen 22. With reference to FIGS. 3 and 4, the main pin 94 has an elongated core 96, and a pair of opposed ears 98a and 98b extending outwardly from the core 96 adjacent a distal end 100 of the main pin 94.

As shown in FIG. 3, a proximal end 102 of an auxiliary pin 104 is inserted into the distal end of the shaft inflation lumen 24 in order to close the distal end of the inflation lumen. As shown, the auxiliary pin 104 has a central portion 105 extending distally from the shaft and aligned with the inflation lumen 24. The pin 104 also has an outwardly turned distal end portion 106 which is spaced from the distal end of the shaft 12, and which is located intermediate the ends of the beveled distal shaft portion.

The distal end 16 of the catheter shaft 12 is placed in a channel 108 of the mold 88 while the main pin 94 and auxiliary pin 104 are placed in the mold cavity 90. In this configuration, the catheter shaft 12 closes the proximal end of the mold cavity 90, while the end portion 106 of the auxiliary pin 104 extends to the wall of the cavity. In addition, the ears 98a and b of the main pin 94 extend to walls of the cavity 90 and support the core 96 and distal end 100 of the main pin 94 at a location spaced from walls of the cavity 90. The end portion 106 of the auxiliary pin 104 and the elongated ear 98b of the main pin 94 are received in a block positioned in recess 110.

After placement of the pins and shaft in the mold 88, a molten material, such as a heated thermoplastic elastomer material, is injected through a gate 112 into the mold cavity 90 to form the cathether tip. The gate 112 is located adjacent the distal end of the shaft in order that the hottest material contacts the shaft and obtains an excellent bond between the shaft and tip. In addition, the gate 112 directs the material against the core 96 in order to spread the material and maintain the desired temperature of the material in the cavity. After the tip has sufficiently cured, the block in recess 110 is utilized to remove the pins and tip from the cavity 90. With reference to FIGS. 2 and 3, the core 96 of the main pin 94 defines the lumen 26 of the tip 14, while the ears 98a and b form the opposed drainage eyes 28 in the tip. The molded tip may be flexed slightly in order to pass the distal end of the tip over the shorter ear 98a. Next, a source of pressurized gas may be connected to the proximal end of the catheter main lumen in order to blow the catheter off the main pin 94 while retained in the block. Hence, the main pin 94 passes through one of the drainage eyes formed in the tip, and at the same time, the auxiliary pin 104, which is also retained by the block, is removed from the cathether through the opening 36. The central portion 105 of the auxiliary pin 104 forms the distal end portion 34 of the inflation lumen in the tip 14, while the distal end portion 106 of the auxiliary pin 104 forms the end of the inflation lumen and the tip aperture 36. Thus, the catheter tip 14 is molded directly onto the distal end of the catheter shaft 12 in a simplified manner while forming the lumen and drainage eyes in the catheter tip. In addition, the auxiliary pin 104 conveniently forms the distal end of the inflation lumen and automatically forms the aperture 36 communicating with the inflation lumen at the outer surface of the tip. The tapered juncture surfaces of the catheter shaft and tip define an enlarged surface area to enhance the bonding strength between the catheter shaft and tip and minimize the possibility of severance during use. As previously indicated, the catheter sleeve 60 may be bonded to the catheter shaft and tip after formation of the tip.

Figure 5:
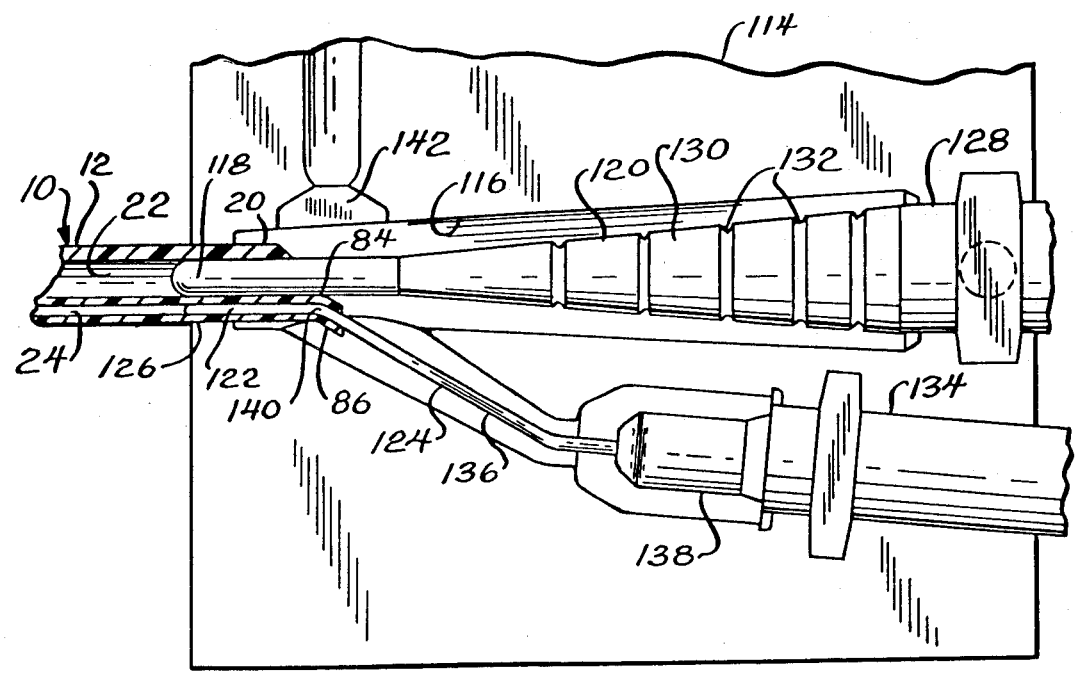
FIG. 5 is a fragmentary plan view of a mold for forming a connecter onto a proximal end of the catheter shaft.

With reference to FIG. 5, a mold 114 is utilized to form the cathether connecter in a cavity 116 as described below. First, the proximal end 20 of the catheter shaft 12 is severed at an angle to form the beveled end portion of the catheter shaft, and the shaft 12 may be also severed along the line 84 to define the flap 86 at the proximal end of the shaft, if desired. Next, the distal end 118 of a main pin 120 is inserted into the proximal end of the shaft main lumen 22 in order to close the proximal end of the shaft lumen 22. In addition, the distal end 122 of an elongated auxiliary pin 124 is inserted into the proximal end of the shaft inflation lumen 24 to close the proximal end of the inflation lumen 24. The proximal end 20 of the catheter shaft 12 is placed in a channel 126 of the mold 114 in order to close the distal end of the cavity 116 while the main pin 120 and auxiliary pin 124 are positioned in the mold cavity 116. In this configuration, a proximal end 128 of the main pin 120 closes the cavity and supports an elongated core 130 of the main pin 120 at a position spaced from walls of the cavity 116. As shown, the main pin core 130 has a plurality of spaced circumferential recesses 132 for a purpose which will be described below. A proximal end 134 of the auxiliary pin 124 closes a proximal end of cavity 116, and supports an elongated central cylindrical section 136 and an enlarged proximal portion 138 at a location spaced from the walls of the cavity 116. In this configuration, a curved portion 140 of the auxiliary pin 124 in the flap 86 retains the flap 86 in an outwardly flared configuration preparatory to forming the connector.

A suitable molten material, such as a thermoplastic elastomer material, is injected through a flared fan gate 142 into the mold cavity 116 in order to form the connecter. The gate 142 is relatively thin in width and has a considerable length, such that the gate 142 spreads the molten material as it passes into the cavity 116. The gate 142 is located adjacent the proximal end of the catheter shaft in order that the hottest material contacts the shaft to achieve an excellent bond between the shaft and connecter. In addition, the gate 142 directs the molten material onto the core 130 of the main pin 120 in order to enhance spreading of the material in the cavity and maintain temperature of the material in the mold. The configuration of the gate 142 also minimizes the scar on the connecter along a thin line after molding has been completed, although the gate 142 is capable of rapidly injecting a large amount of material into the cavity.

After the connecter has sufficiently cured, the catheter and pins are removed from the cavity. With reference to FIGS. 2 and 5, the core 130 of the main pin 120 forms the main lumen 42 of the connecter 18 while the recesses 132 form the connecter sealing rings 44. The main pin 120 may be removed through an opening formed at the proximal end of the connecter 18 while the auxiliary pin 124 may also be removed by flexing the side arm 46 of the connecter 18 slightly and drawing the auxiliary pin through an opening at the proximal end of the side arm. The central section 136 of the auxiliary pin 124 forms the inflation lumen 48 in the connecter side arm, while the enlarged proximal portion 138 of the auxiliary pin 124 forms the recess 50 for the valve means. As constructed, the connecter flange 56 surrounds and encloses the proximal end 20 of the catheter shaft 12. In addition, the connecter 18 has material extending around the proximal shaft flap 86 surrounding the proximal end of the inflation lumen while the outwardly flared flap 86 in the connecter 18 assures continuity and integrity between the inflation lumen 24 of the shaft 12 and the inflation lumen 48 of the connecter side arm 46. The tapered juncture surfaces of the shaft and connecter provide additional surface area to enhance the bond strength between the catheter shaft 12 and connecter 18.

Thus, in this manner the catheter tip and connecter may be formed and bonded to the catheter shaft in a molding operation which assures simplicity in the manufacturing process of the catheter while achieving an excellent bond between the tip and connecter and the catheter shaft. With reference to FIG. 6, it will be seen that the proximal and distal ends 20 and 16 of the catheter shaft 12 may be inserted into the tip mold 88 and connecter mold 114 in order to simultaneously insert mold the catheter shaft onto the catheter tip and connecter. Of course, the cavities for the tip and connecter may be placed in a single mold for simultaneous molding of the tip and connecter to the catheter shaft in one mold, if desired.

The foregoing detailed description is given for clearness of understanding only, and no unnecessary limitations should be understood therefrom, as modifications will be obvious to those skilled in the art.

We claim:

1. In a method of making a catheter, comprising the steps of:

severing a proximal end of a catheter shaft and forming a taper in the proximal end of the catheter shaft;

inserting a distal end of a main pin into a proximal end of a main lumen in the catheter shaft and closing the proximal end of the main lumen with the main pin;

inserting said distal end of an auxiliary pin into a proximal end of an inflation lumen in a wall of the shaft and closing the proximal end of the inflation lumen with the auxiliary pin;

placing the proximal end of the catheter shaft and said main and auxiliary pins into a mold cavity with a core portion of the main pin and an elongated proximal portion of the auxiliary pin being spaced from walls of the mold, and with a proximal end portion of the catheter shaft containing the proximal end of the drainage lumen being outwardly flared in the mold;

injecting a molten material into the cavity to mold a connecter directly onto the proximal end of the shaft;

removing the main pin through an opening formed by the main pin at the proximal end of the connecter with said core portion forming a lumen in the connecter communicating with the main lumen of the shaft; and removing the auxiliary pin through an opening formed by the auxiliary pin at a proximal portion of the connecter, with the auxiliary pin forming an inflation lumen in the connecter, and with said proximal end portion of the shaft defining a curved portion of the shaft inflation lumen communicating between the shaft and connecter inflation lumens.

2. In a method of making a catheter, comprising the steps of:

severing a proximal end of a catheter shaft and forming a flap containing a proximal end of an inflation lumen to define an outwardly flared shaft end portion;

inserting a distal end of a main pin into a proximal end of a main lumen in the catheter shaft and closing the proximal end of the main lumen with the main pin;

inserting a distal end of an auxiliary pin into a proximal end of the inflation lumen in a wall of the shaft and closing the proximal end of the inflation lumen with the auxiliary pin;

placing said proximal end of the catheter shaft and said main and auxiliary pins into a mold cavity with a core portion of the main pin and an elongated proximal portion of the auxiliary pin being spaced from walls of the mold, and with the proximal end portion of the catheter shaft containing the proximal end of the drainage lumen being outwardly flared in the mold;

injecting a molten material into the cavity to mold a connecter directly onto the proximal end of the shaft;

removing the main pin through an opening formed by the main pin at the proximal end of the connecter with said core portion forming a lumen in the connecter communicating with the main lumen of the shaft; and removing the auxiliary pin through an opening formed by the auxiliary pin at a proximal portion of the connecter, with the auxiliary pin forming an inflation lumen in the connecter, and with said proximal end portion of the shaft defining a curved portion of the shaft inflation lumen communicating between the shaft and connecter inflation lumens.

3. The method of claim 2 including the step of forming a taper in the proximal end of the shaft with an acute angle formed by said taper being located at the proximal end of said flap.

4. The method of claim 2 including the step of forming a taper in the proximal end of the shaft with an acute angle formed by said taper being located at the shaft end portion.

5. The method of claim 2 wherein said injecting step comprises the step of directing the molten material into the cavity at a location adjacent the distal end of the shaft.

6. The method of claim 2 wherein said injecting step comprises the step of directing the molten material against the core portion.

7. The method of claim 2 wherein said injecting step comprises the step of spreading the molten material as it enters the cavity.

8. In a method of making a catheter, comprising the steps of:

severing a distal end of a catheter shaft and forming a taper in the distal end of the catheter shaft;

inserting a proximal end of a main pin into a distal end of a main lumen in the catheter shaft closing the distal end of the main lumen with the main pin;

placing said distal end of the catheter shaft and said main pin into a mold cavity with a core of the main pin being spaced from walls of the cavity, and with a supporting portion of the main pin extending to walls of the cavity adjacent a distal end of the main pin;

injecting a molten material into the cavity to mold a tip directly onto the distal end of the shaft;

removing the shaft and formed tip from the mold cavity; and removing the main pin through an opening defined by said supporting portion in the tip, with said core defining a lumen in the tip communicating between said main lumen and tip opening.

9. The method of claim 8 wherein the forming step forms an obtuse angle in the catheter shaft adjacent the distal end of the inflation lumen.

10. The method of claim 8 wherein the distal portion of the auxiliary pin is located intermediate ends of the shaft tapered portion.

11. The method of claim 8 including the step of forming a taper in the distal end of the catheter shaft.

12. The method of claim 8 wherein said injecting step comprises the step of directing the molten material into the cavity at a location adjacent the distal end of the shaft.

13. The method of claim 8 wherein said injecting step comprises the step of directing the molten material against the core.

14. The method of claim 8 wherein the second removing step comprises the step of passing fluid into a proximal end of the catheter shaft.

15. The method of claim 8 including the step of inserting a proximal end of an auxiliary pin into a distal end of an inflation lumen in a wall of the shaft and closing the distal end of the inflation lumen with the auxiliary pin with a distal portion of the auxiliary pin extending to a wall of the cavity proximal said connecting portion of the main pin.

16. The method of claim 15 including the step of removing the auxiliary pin through an aperture defined by the auxiliary pin at an outer surface of the tip.

17. The method of claim 16 including the step of securing an elastic sleeve to the catheter in spaced circumferential zones with the sleeve defining a cavity communicating with said aperture.

* * * * *